US012691187B2

(12) United States Patent
Lei et al.

(10) Patent No.: US 12,691,187 B2
(45) Date of Patent: Jul. 28, 2026

(54) FAST HARMLESS TREATMENT DEVICE FOR HAZARDOUS FLEXIBLE MATERIAL

(71) Applicant: WESTLAKE UNIVERSITY,
Hangzhou (CN)

(72) Inventors: Liang Lei, Hangzhou (CN); Jinbo Jia,
Hangzhou (CN); Yongke Zheng,
Hangzhou (CN); Zhiyang Hu,
Hangzhou (CN); Yujia Zhang,
Hangzhou (CN); Weicheng Cui,
Hangzhou (CN); Zixu Liu, Hangzhou
(CN); Wenjie Xu, Hangzhou (CN)

(73) Assignee: WESTLAKE UNIVERSITY,
Hangzhou (CN)

( * ) Notice: Subject to any disclaimer, the term of this patent is extended or adjusted under 35 U.S.C. 154(b) by 376 days.

(21) Appl. No.: 18/539,292

(22) Filed: Dec. 14, 2023

(65) Prior Publication Data

US 2024/0299602 A1 Sep. 12, 2024

Related U.S. Application Data

(63) Continuation of application No. PCT/CN2023/114141, filed on Aug. 22, 2023.

(30) Foreign Application Priority Data

Mar. 10, 2023 (CN) .......................... 202310228682.0

(51) Int. Cl.
| | |
|---|---|
| *A61L 2/04* | (2006.01) |
| *A61L 2/26* | (2006.01) |
| *B65D 25/10* | (2006.01) |
| *B65D 25/24* | (2006.01) |
| *B65D 43/16* | (2006.01) |

(Continued)

(52) U.S. Cl.
CPC *A61L 2/04* (2013.01); *A61L 2/26* (2013.01); *B65D 25/10* (2013.01); *B65D 25/24* (2013.01); *B65D 43/163* (2013.01); *B65D 51/24* (2013.01); *B65D 81/3802* (2013.01); *A61L 2103/50* (2026.01); *A61L 2202/11* (2013.01); *A61L 2202/122* (2013.01); *B65D 2543/00092* (2013.01); *B65D 2543/00842* (2013.01)

(58) Field of Classification Search
CPC ....................................................... A61L 2/04
See application file for complete search history.

(56) References Cited

FOREIGN PATENT DOCUMENTS

| | | |
|---|---|---|
| CN | 211751296 U | 10/2020 |
| CN | 112472833 A | 3/2021 |

(Continued)

*Primary Examiner* — Donald R Spamer
(74) *Attorney, Agent, or Firm* — Bayramoglu Law Offices LLC

(57) ABSTRACT

A fast harmless treatment device for a hazardous flexible material is provided. The fast harmless treatment device includes a container body and a container lid, where a bottom plate is fixed at a near-bottom position of the container body; a movable plate is provided in the container body; there is a gap between an outer edge of the movable plate and an inner wall of the container body; a movement mechanism is configured to compress a hazardous flexible material on the movable plate towards the container lid; the container lid and the movable plate each are provided therein with a heating tube; and a heating tube and a blowing device are provided on the bottom plate to cause high-temperature convection and disinfect an aerosol-mixed gas.

6 Claims, 5 Drawing Sheets

(51) Int. Cl.
    B65D 51/24       (2006.01)
    B65D 81/38       (2006.01)
    *A61L 103/50*      (2026.01)

(56)            References Cited

FOREIGN PATENT DOCUMENTS

| CN | 112472858 | A | 3/2021 |
|----|-----------|---|--------|
| CN | 214242372 | U | 9/2021 |
| CN | 216965772 | U | 7/2022 |
| CN | 114833168 | A | 8/2022 |
| CN | 217550725 | U | 10/2022 |
| CN | 115252840 | A | 11/2022 |
| CN | 115502178 | A | 12/2022 |
| CN | 115889421 | A | 4/2023 |
| EP | 0645304 | A1 | 3/1995 |
| JP | 2001029917 | A | 2/2001 |
| JP | 2001299301 | A | 10/2001 |

FAST HARMLESS TREATMENT DEVICE FOR HAZARDOUS FLEXIBLE MATERIAL

CROSS REFERENCE TO THE RELATED APPLICATIONS

This application is a continuation application of International Application No. PCT/CN2023/114141, filed on Aug. 22, 2023, which is based upon and claims priority to Chinese Patent Application No. 202310228682.0, filed on Mar. 10, 2023, the entire contents of which are incorporated herein by reference.

TECHNICAL FIELD

The present disclosure belongs to the field of high-temperature disinfection equipment, and in particular to a fast harmless treatment device for a hazardous flexible material.

BACKGROUND

Hazardous flexible materials (including masks, protective clothing, or fabrics in contact with infectious disease patients) are typically divided into two categories: disposable and reusable. Disposable hazardous flexible materials need to be collected and destroyed in a centralized manner. Reusable hazardous flexible materials require disinfection of bacteria, viruses, and other microorganisms adhered before reuse.

Disposable hazardous flexible materials are fluffy after use and not suitable for compression during on-site collection and transfer, resulting in low storage efficiency, high costs, and risks.

The mainstream disinfection solutions for reusable hazardous flexible materials include ultraviolet radiation, high-pressure steam, disinfectants, etc.

Chinese patent application CN115252840A provides an ultraviolet disinfection box for protective clothing. The ultraviolet disinfection box utilizes ultraviolet radiation to irradiate microorganisms such as bacteria and viruses in order to destroy the structure of deoxyribonucleic acid (DNA) in the microbial body, thereby causing the microorganisms to immediately die or lose their reproductive ability, so as to achieve sterilization.

Chinese patent application CN112472833A provides a harmless treatment device for infectious disease protective clothing. The harmless treatment device utilizes steam disinfection and allows the protective clothing to rotate during steam disinfection in order to ensure complete disinfection of the protective clothing.

Chinese patent application CN112472858A provides a comprehensive disinfection device for protective clothing that is designed to disinfect the protective clothing through an appropriate mixture of different disinfectants.

However, ultraviolet disinfection is generally only applicable to a single protective consumable and can only irradiate the surface of the consumable without interior, failing to perform well when dealing with more than a single consumable. The high-pressure steam equipment is bulky and needs to be combined with water for use, resulting in low disinfection efficiency, high energy consumption, and limited use scenarios. As for spraying disinfection, the disinfectant represented by alcohol can only act on the surface of the consumable simply and cannot evenly spray or disinfect the interior of the consumable. The soaking disinfection method requires a large amount of chemicals, and there will be a large amount of chemical residue on the treated material, affecting subsequent incineration or reuse. In summary, the surface disinfection equipment ignores disinfection of the hazardous aerosol inside the hazardous material, so there is a hidden danger, while the overall disinfection equipment is bulky, time-consuming, unfriendly to subsequent treatment, and unsuitable for on-site rapid disinfection.

Overall, there is currently no efficient solution on the market for the on-site harmless treatment of hazardous flexible materials.

SUMMARY

The present disclosure provides a fast harmless treatment device for a hazardous flexible material. The present disclosure is applicable to disposable and reusable materials. The present disclosure ensures complete inactivation of viruses at a surface and interior of the hazardous flexible material and viruses in air inside a chamber in a high-temperature environment. In addition, the present disclosure compresses the volume of the hazardous flexible material while eliminating a subsequent pollution risk. Therefore, the present disclosure effectively improves the efficiency of harmless treatment, significantly reduces the consumption of manpower and material resources, and reduces the risk of virus transmission during transfer and centralization.

Technical solutions of the present disclosure are as follows:

A fast harmless treatment device for a hazardous flexible material includes a container body and a container lid, where a bottom plate is fixed at a near-bottom position of the container body; a movable plate controlled by a movement mechanism to move up and down is provided in the container body; there is a gap between an outer edge of the movable plate and an inner wall of the container body; and the movement mechanism is configured to compress a hazardous flexible material on the movable plate towards the container lid and cause an aerosol generated after compression to flow down along the gap between the movable plate and the inner wall of the container body; and the container lid and the movable plate each are provided therein with a heating tube for performing high-temperature disinfection on the hazardous flexible material in the container body, concurrently with compression of the hazardous flexible material; and a heating tube and a blowing device are provided on the bottom plate to cause high-temperature convection in a chamber between the movable plate and the bottom plate and disinfect an aerosol-mixed gas generated after compression of the hazardous flexible material.

In the technical solution of the present disclosure, mechanical compression is performed on the hazardous flexible material. After compression, the thermal conductivity of the hazardous flexible materials is significantly improved. The temperature of the heating tubes inside the movable plate and the container lid is raised, such that the surface and interior of the hazardous flexible material between the plates can quickly reach a disinfection temperature. The heating tube on the bottom plate cooperates with the blowing device to conduct convection heating disinfection on the aerosol with potential pathogenic microorganisms generated after compression of the hazardous flexible material. The whole disinfection process is carried out under a sealed condition to ensure a safe and no-leakage disinfection process, and the disinfected hazardous flexible material occupies small space and is convenient for storage and transfer.

In the present disclosure, the movement mechanism can be in various forms to drive the movable plate to move up and down and achieve mechanical compression of the hazardous flexible material when driving the movable plate towards the container lid.

In a preferred structure, the movement mechanism includes at least one linear motor vertically fixed to an inner bottom surface of the container body and a screw rod with a lower end connected to an output shaft of the linear motor and an upper end rotatably fixed to a fixing ring provided at an upper end of the container body; at least one guide rod running through the movable plate is provided between the inner bottom surface of the container body and the fixing ring; the movable plate is matched with the screw rod through an internally threaded screw rod sleeve; and the screw rod is driven by a motor to move the movable plate up and down along the guide rod.

In the movement mechanism, there can be two linear motors corresponding to two screw rods. The two linear motors synchronously drive the two screw rods through a transmission assembly, causing the two screw rods to rotate synchronously. There can also be two guide rods. The screw rods and the guide rods are evenly and alternately arranged along a circumference of the movable plate.

In the present disclosure, the blowing device can be in various forms to achieve heated air circulation within the container body.

In a preferred structure, the blowing device includes a motor and a blade; the motor is sealed and fixed at a center of a lower end surface of the bottom plate; and an output shaft of the motor passes through the bottom plate and is connected to the blade above. The preferred structure can provide thermal protection for the blowing motor, effectively reduce disinfection energy consumption and increase the temperature rise rate in the container body.

Further, a control panel is provided outside the container body, for controlling the heating of the heating tube, the up-down movement of the movable plate, and the on-off of the blowing device.

Further, a lower surface of the container lid, an upper surface of the movable plate, an upper surface of the bottom plate, and an interior of the container body are provided with temperature sensors; the temperature sensors are monitored through the control panel in real time; and a proportional-integral-derivative (PID) control module is combined to control the heating tubes separately, thereby achieving automatic temperature control and maintaining a constant temperature over a targeted period of time.

Preferably, an outer bottom surface of the container body is provided with multiple swivel casters to facilitate the movement of the entire treatment device. Before on-site disinfection, the fast harmless treatment device is moved to a stable ground and locking buckles of the swivel casters are pressed to ensure the stability of the fast harmless treatment device during disinfection.

Preferably, the container lid is provided with a clamshell structure; the container lid is fixed to a sealing flange provided at the upper end of the container body through a fastener; and the container lid is provided with an opening handle.

Preferably, the container body is a cylinder or square column in shape; and the inner wall of the container body is provided with an insulation layer.

Compared with the prior art, the present disclosure has the following beneficial effects:

1. In the present disclosure, the whole disinfection process of the fast harmless treatment device is carried out under a sealed condition, and the aerosol generated after compression of the material and the inner wall of the sealed chamber disinfected at a high temperature, thereby ensuring a safe and no-leakage disinfection process.

2. The present disclosure uses a high-temperature method to disinfect potential pathogenic microorganisms. This method is safe, and has low energy consumption. In addition, the whole process does not need a chemical reagent, making the fast harmless treatment device economical and environmentally friendly.

3. The present disclosure provides a low-temperature disinfection mode to treat reusable materials and a high-temperature disinfection mode to treat disposable materials, improving the disinfection efficiency.

4. The present disclosure performs mechanical compression while disinfecting the hazardous flexible material, such that the hazardous flexible material takes up less space after disinfection, easing storage and transfer, and saving treatment costs. Under the condition that a relevant standard is met, the disinfected medical hazardous material can be treated as ordinary garbage, which greatly reduces the cost.

5. The present disclosure has a wide range of application scenarios, including but not limited to large-scale event venues, hotels, hospitals, schools, and home environments.

Reference Signs: 1. container body; 2. container lid; 21. container lid heating tube; 3. bottom plate; 31. bottom plate heating tube; 4. movable plate; 41. movable plate heating tube; 5. linear motor; 6. screw rod; 7. guide rod; 8. blowing device; 81. motor; 82. blade; 9. fixing ring; 10. swivel caster; 11. opening handle; 12. control panel; 13. hazardous flexible material; and 14. container body shell.

DETAILED DESCRIPTION OF THE EMBODIMENTS

The present disclosure is further described in detail below with reference to the drawings and embodiments. It should be noted that the following embodiments are for the ease of understanding, rather than limiting.

The following described is one of the forms. The shape of the container body, the mechanical compression mode of the movement mechanism, the heating mode of high-temperature disinfection and the specific structure of the blowing device can be implemented in many forms, not limited to the following description.

Figure 1:
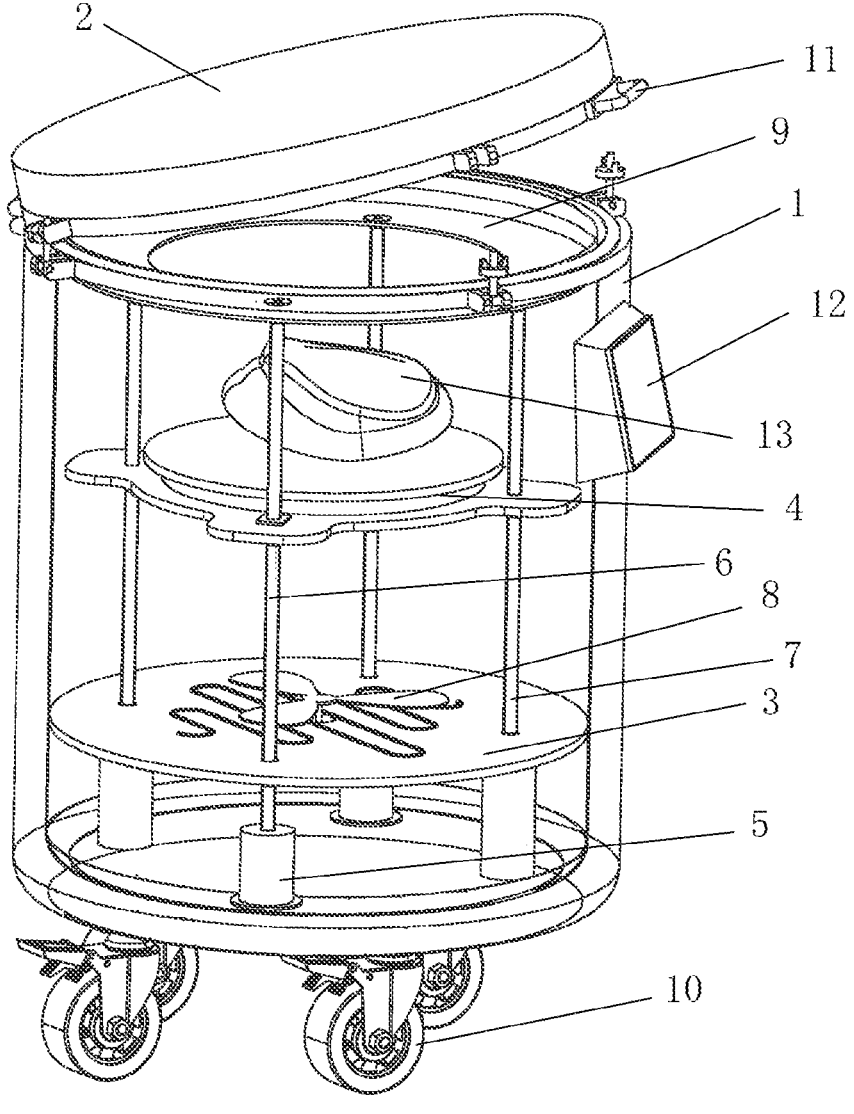
FIG. 1 is an overall structural diagram of a fast harmless treatment device for a hazardous flexible material according to the present disclosure.
Figure 2:
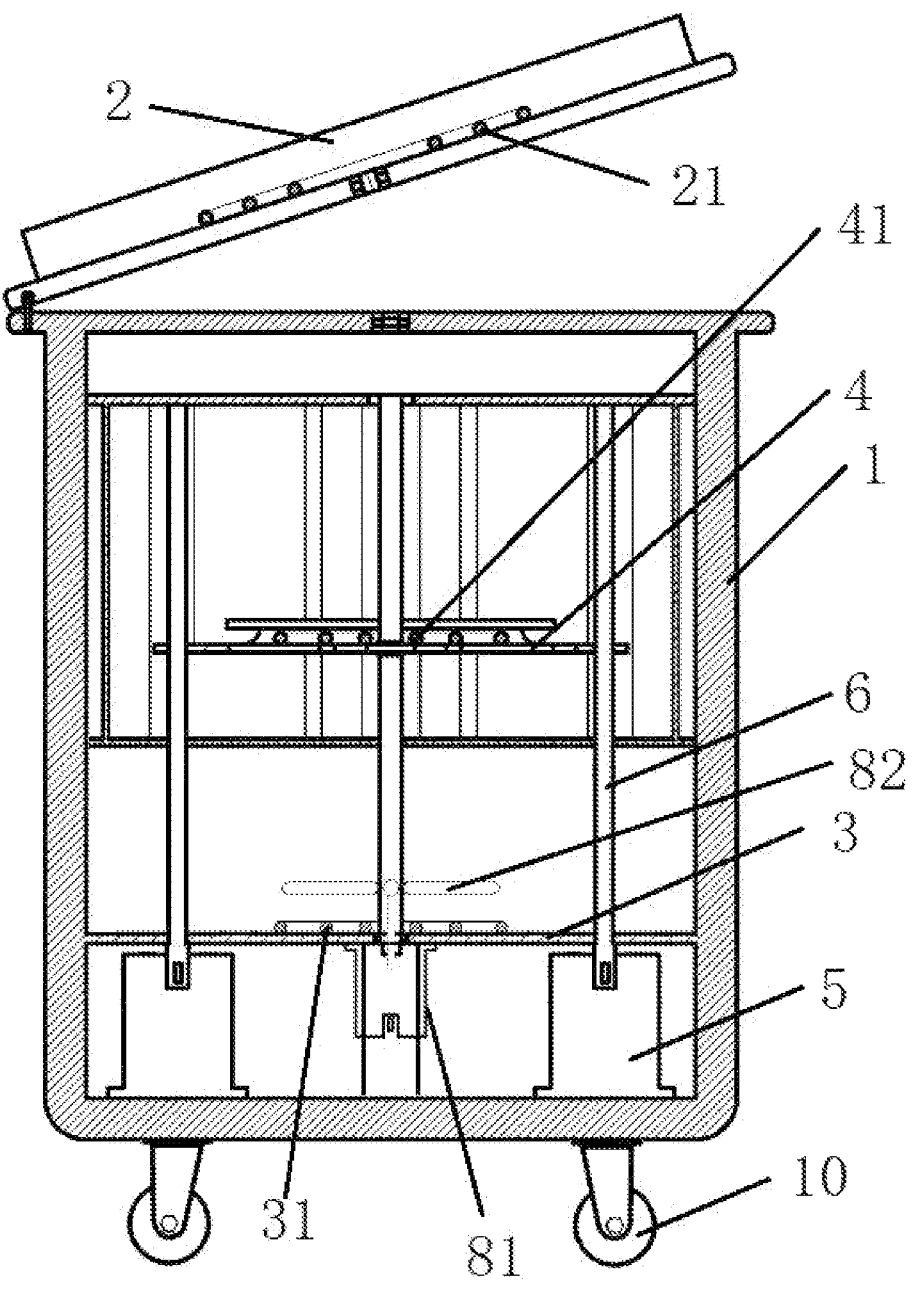
FIG. 2 is a section view of the fast harmless treatment device for a hazardous flexible material according to the present disclosure.
Figure 3:
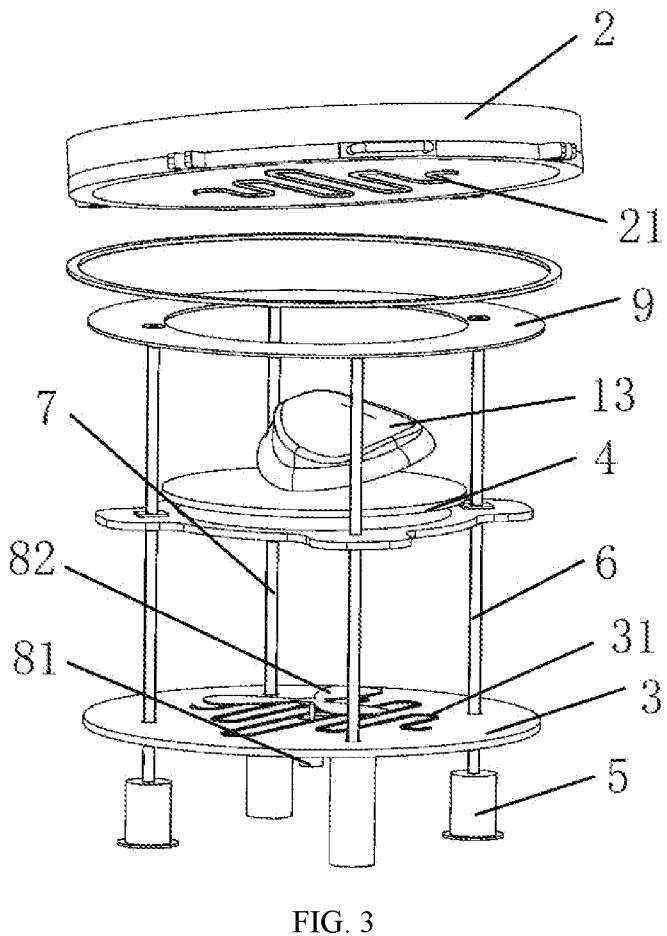
FIG. 3 is a schematic diagram of a bottom plate, a movable plate, and a container lid that are matched with each other according to the present disclosure.

As shown in FIGS. 1 to 3, a fast harmless treatment device for a hazardous flexible material includes container body 1 and container lid 2. The container lid 2 is provided with a clamshell structure. The container lid 2 is fixed to a sealing flange provided at an upper end of the container body 1 through a fastener. The container lid 2 is provided with opening handle 11.

Bottom plate 3 is fixed at a near-bottom position of the container body 1, and movable plate 4 controlled by a movement mechanism to move up and down is provided in the container body.

The container lid 2 is provided therein with a heating plate. The heating plate is provided with container lid heating tube 21. The movable plate 4 is provided with movable plate heating tube 41 for high-temperature disinfection of a hazardous flexible material in the container body. Bottom plate heating tube 31 is provided on the bottom plate 3 for high-temperature disinfection of an aerosol-mixed gas in the barrel body. There is a gap between an outer edge of the movable plate 4 and an inner wall of the container body 1. The movement mechanism is configured to compress the hazardous flexible material 13 on the movable plate 4 towards the container lid 2, and to cause the generated aerosol to flow down along the gap between the movable plate 4 and the inner wall of the container body 1. The bottom plate 3 is provided with blowing device 8 for causing high-temperature convection of the aerosol-mixed gas in a chamber between the movable plate and the bottom plate after the hazardous flexible material is compressed. In this embodiment, the movement mechanism includes two linear motors 5 vertically fixed to a support on an inner bottom surface of the container body 1, screw rods 6 with respective lower ends connected to output shafts of the two linear motors 5 and upper ends rotatably fixed to fixing ring 9 provided at the upper end of the container body. Two guide rods 7 running through the movable plate 4 are provided between the inner bottom surface of the container body 1 and the fixing ring 9. The movable plate 4 is provided with guide rod fixing sleeves matched with the guide rods 7. The screw rods 6 and the guide rods 7 are evenly and alternately arranged along a circumference of the movable plate 4.

The movable plate 4 is matched with the screw rods 6 through internally threaded screw rod sleeves. The two linear motors 5 synchronously drive the two screw rods 6 through a transmission assembly, causing the two screw rods 6 to rotate synchronously, thereby driving the movable plate 4 to move up and down along the guide rods. The internally threaded screw rod sleeves are provided at two ends of the heating plate, for driving the heating plate to move up and down in parallel. Upper ends of the screw rods 6 and the guide rods 7 are concentrically positioned through the fixing ring 9 connected to the wall of the container body to maintain vertical rotation during operation.

The blowing device 8 includes motor 81 and blade 82. The motor 81 is fixed at a center of a lower end surface of the bottom plate 3, and an output shaft of the motor 81 passes through the bottom plate 3 and is connected to the blade 82 above.

Figure 5:
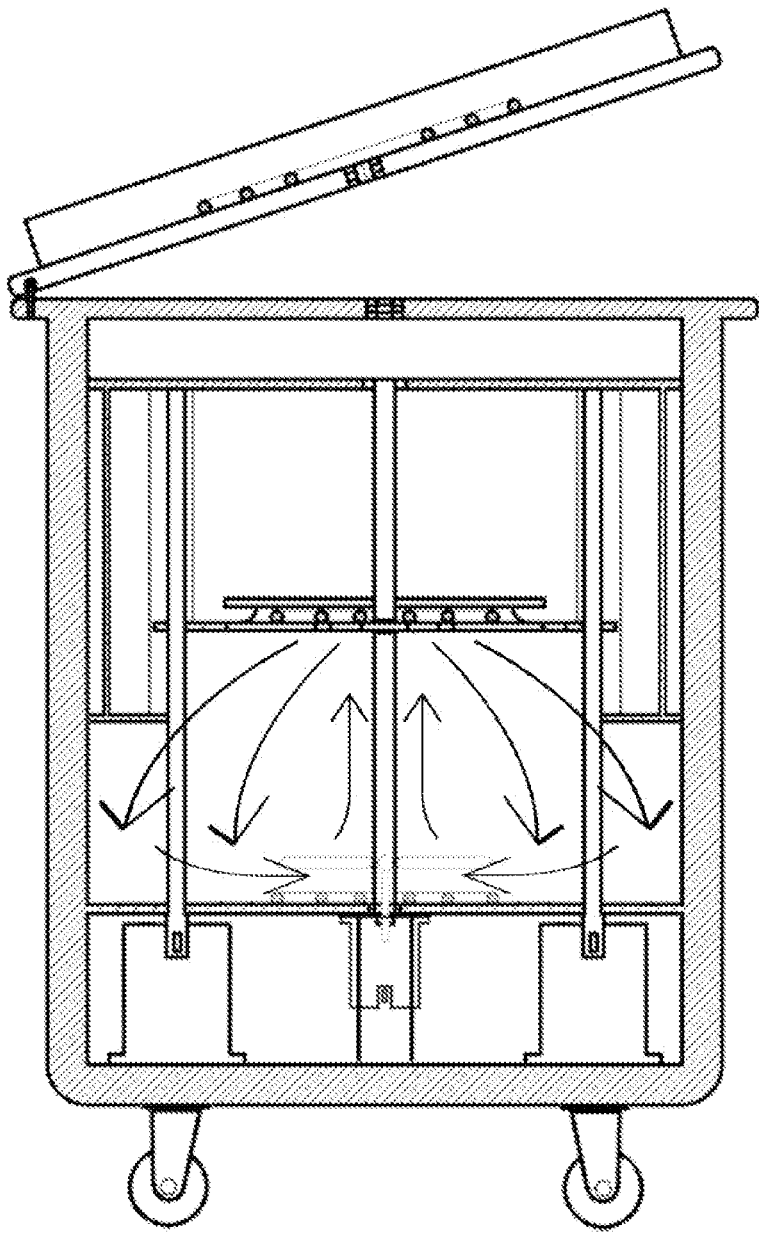
FIG. 5 is a schematic diagram of air circulation in the container body according to an embodiment of the present disclosure.

During a disinfection cycle, the hazardous flexible material 13 is gradually compacted between the movable plate 4 and the container lid 2. After the hazardous flexible material 13 is compressed, its thermal conductivity is significantly improved. The movable plate heating tube 41 and the container lid heating tube 21 are heated to make a surface and interior of the hazardous flexible material between the two plates reach a disinfection temperature quickly. The bottom plate heating tube 31 and the blowing device 8 cause convection heating disinfection for the air with potential pathogenic microorganisms in the chamber of the container body. The process of cyclic convection is shown in FIG. 5.

In this embodiment, the container body 1 is a cylindrical structure, with an outer shell made of a heat-resistant plastic. Control panel 12 is provided outside the container body 1, for controlling the heating of the heating tube, the up-down movement of the movable plate 4, and the on-off of the blowing device 8. A lower surface of the container lid 2, an upper surface of the movable plate 4, an upper surface of the bottom plate 3, and the interior of the container body 1 are provided with temperature sensors. The temperature sensors are monitored through the control panel 12 in real time, and a proportional-integral-derivative (PID) control module is combined to achieve automatic temperature control and maintaining a constant temperature over a targeted period of time.

Figure 4:
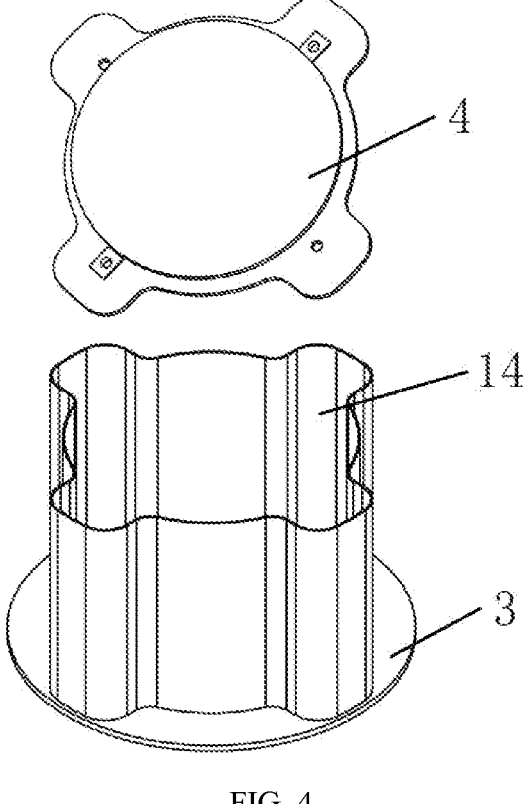
FIG. 4 is a schematic diagram of the movable plate and an inner wall of a container body that are matched with each other according to the present disclosure.

In order to ensure the heating efficiency and safety of the fast harmless treatment device, it is necessary to provide an insulation boundary around an internal heating area of the fast harmless treatment device. For this purpose, the container body 1 is provided therein with a heat-resistant plastic container body shell, which separates the internal heating area from the container wall, and an insulation material is provided between the internal heating area and the container wall. As shown in FIG. 4, the container body shell 14 is in a shape matched with that of the movable plate 4.

A working principle and operating steps of the present disclosure are as follows.

Step 1. A bottom of the fast harmless treatment device is provided with adjustable swivel casters 10. Before on-site disinfection, the fast harmless treatment device is moved to a stable ground and locking buckles of the swivel casters are pressed to ensure the stability of the fast harmless treatment device during disinfection. The fast harmless treatment device is connected to a power source. A start button on the control panel 12 is pressed. The clamshell container lid 2 is closed, and a preheating button is clicked to preheat the three heating tubes inside the fast harmless treatment device. The preheating function can increase the plate temperature and air temperature to 50-60° C. The fast harmless treatment device is provided with heating tubes on the lid plate, the movable plate, and the bottom plate. The blowing device 8 on the bottom plate causes convection heating for the air inside the chamber. The temperature sensors inside the lid plate, the movable plate, the bottom plate, and the chamber are monitored in real time through the control panel 12. A PID control system is combined to achieve automatic temperature control and maintaining a constant temperature over a targeted period of time.

Step 2. After the preheating is finished, the container lid 2 of the fast harmless treatment device is opened. The hazardous flexible material 13 is put into the fast harmless treatment device, and the container lid 2 is closed. The sealing flange 6 at the upper end of the container body 1 is provided with the sealing ring, and the fastener on the edge of the container lid 2 is tightened to seal the chamber of the container body 1. An operator who opens the container lid 2 and putting the hazardous flexible material into the container body should wear heat-resistant gloves.

Step 3. A disinfection mode is selected on the control panel 12, such as a low-temperature reuse mode and a high-temperature fast disinfection mode. The start button is clicked to turn on the heating tubes and the blowing device simultaneously. The system controls a maximum temperature of the lower surface of the container lid, the upper surface of the movable plate, the upper surface of the bottom plate, and the air in the container body not to exceed a set value according to the selected disinfection mode. The linear motors 5 drive the screw rods 6 to rotate, thereby driving the movable plate 4 to move up. The hazardous flexible material 13 is compressed between the movable plate 4 and the container lid 2 until it is compacted. The movable plate 4 automatically stops under the feedback control of the linear motors 5. Most of the aerosols inside the hazardous flexible material 13 flow down into the chamber along the gap between the movable plate 4 and the inner wall of the container body. The air flow generated by the blowing device 8 causes high-temperature convection of the aerosol-mixed gas in the chamber between the movable plate 4 and the bottom plate 3.

After the real-time temperatures of the lower surface of the container lid, the upper surface of the movable plate, the upper surface of the bottom plate, and the air reach set temperatures, the temperatures are held for a certain period of time (specifically determined by the disinfection mode, generally not more than 5 min). The design ensures that the viruses at surface and interior positions of the hazardous flexible material, as well as in the air inside the chamber, are completely inactivated in a high-temperature environment.

Step 4. After the disinfection is finished, the heating tubes are stopped. A pressure relief valve of the container body is started to relieve a possible high pressure in the sealed chamber, and the system prompts that disinfection is completed. The container lid 2 is opened, and the disinfected hazardous flexible material is taken out and stored for centralized treatment. A reset button on the control panel is pressed, and the pressure relief valve is automatically closed. The heating plate is moved down to the bottom.

Step 5. The fast harmless treatment device can be used continuously during on-site disinfection. After a disinfection cycle is completed, another hazardous flexible material for disinfection can be put into the chamber for disinfection according to steps 2 to 4. An operator who removes and puts the hazardous flexible material should wear heat-resistant gloves.

The technical solutions and beneficial effects of the present disclosure are described in detail in the above embodiments. It should be understood that the above embodiments are merely specific embodiments of the present disclosure and are not intended to limit the present disclosure. Any modification, supplement, and equivalent replacement made within the principle scope of the present disclosure should fall within the protection scope of the present disclosure.

What is claimed is:

1. A treatment device for a hazardous flexible material, comprising a container body and a container lid, wherein a bottom plate is fixed at a near-bottom position of the container body; a movable plate is provided in the container body, wherein the movable plate is controlled by a movement mechanism to move up and down; a gap is formed between an outer edge of the movable plate and an inner wall of the container body; and the movement mechanism is configured to compress a hazardous flexible material on the movable plate towards the container lid and cause an aerosol-mixed gas generated after compression to flow down along the gap between the movable plate and the inner wall of the container body;

the container lid is provided therein with a first heating tube and the movable plate is provided with a second heating tube for performing high-temperature disinfection on the hazardous flexible material in the container body, concurrently with compression of the hazardous flexible material; and a third heating tube and a blowing device are provided on the bottom plate to cause high-temperature convection in a chamber between the movable plate and the bottom plate and disinfect the aerosol-mixed gas generated after the compression of the hazardous flexible material;

the movement mechanism comprises two linear motors vertically fixed to an inner bottom surface of the container body and two screw rods with respective lower ends connected to output shafts of the two linear motors and upper ends rotatably fixed to a fixing ring, wherein the fixing ring is provided at an upper end of the container body; the two linear motors synchronously drive the two screw rods through a transmission assembly, causing the two screw rods to rotate synchronously; two guide rods are provided between the inner bottom surface of the container body and the fixing ring, wherein the two guide rods runs through the movable plate; the two screw rods and the two guide rods are evenly and alternately arranged along a circumference of the movable plate; the movable plate is matched with the two screw rods through internally threaded screw rod sleeves; and the two screw rods are driven by the two linear motors to move the movable plate up and down along the two guide rods; and the blowing device comprises a motor and a blade; the motor is sealed and fixed at a center of a lower end surface of the bottom plate; and an output shaft of the motor passes through the bottom plate and is connected to the blade above.

2. The treatment device for the hazardous flexible material according to claim 1, wherein a control panel is provided outside the container body, for controlling heating of the first heating tube, the second heating tube, and the third heating tube, an up-down movement of the movable plate, and an on-off of the blowing device.

3. The treatment device for the hazardous flexible material according to claim 1, wherein a lower surface of the container lid, an upper surface of the movable plate, an upper surface of the bottom plate, and an interior of the container body are provided with temperature sensors; the temperature sensors are monitored through a control panel in real time; and a proportional-integral-derivative (PID) control module is combined to achieve automatic temperature control and maintaining a constant temperature over a targeted period of time.

4. The treatment device for the hazardous flexible material according to claim 1, wherein an outer bottom surface of the container body is provided with a plurality of swivel casters.

5. The treatment device for the hazardous flexible material according to claim 1, wherein the container lid is provided with a clamshell structure; the container lid is fixed to a sealing flange provided at the upper end of the container body through a fastener; and the container lid is provided with an opening handle.

6. The treatment device for the hazardous flexible material according to claim 1, wherein the container body is a cylinder or square column in shape; and the inner wall of the container body is provided with an insulation layer.

* * * * *